(12) United States Patent
Kast et al.

(10) Patent No.: US 7,798,862 B2
(45) Date of Patent: Sep. 21, 2010

(54) MEDICAL ELECTRICAL LEAD CONNECTION SYSTEMS AND METHODS

(75) Inventors: John Kast, Hugo, MN (US); Mark Lent, Brooklyn Park, MN (US); James Olsen, Plymouth, MN (US); Andrew Ries, Lino Lakes, MN (US); James Skakoon, St. Paul, MN (US); Carl Wahlstrand, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/482,033

(22) Filed: Jun. 10, 2009

(65) Prior Publication Data

US 2009/0247018 A1 Oct. 1, 2009

Related U.S. Application Data

(63) Continuation of application No. 12/140,877, filed on Jun. 17, 2008, now Pat. No. 7,553,193, which is a continuation of application No. 11/689,531, filed on Mar. 22, 2007, now Pat. No. 7,402,083.

(60) Provisional application No. 60/785,194, filed on Mar. 23, 2006.

(51) Int. Cl.
*H01R 24/00* (2006.01)
(52) U.S. Cl. .................................. 439/660; 439/909
(58) Field of Classification Search ................. 439/660, 439/909, 668, 409
See application file for complete search history.

(56) References Cited

U.S. PATENT DOCUMENTS

| | | | |
|---|---|---|---|
| 4,469,104 A | 9/1984 | Peers-Trevarton | |
| 4,712,557 A | 12/1987 | Harris | |
| 4,869,255 A | 9/1989 | Putz | |
| 5,046,242 A * | 9/1991 | Kuzma | .................... 29/878 |
| 5,354,326 A | 10/1994 | Comben et al. | |
| 5,560,358 A | 10/1996 | Arnold et al. | |
| 5,947,761 A | 9/1999 | Pepe | |
| 6,162,101 A | 12/2000 | Fischer et al. | |
| 6,321,126 B1 | 11/2001 | Kuzma | |
| 6,415,168 B1 | 7/2002 | Putz | |
| 6,575,793 B1 | 6/2003 | Li et al. | |
| 6,662,035 B2 | 12/2003 | Sochor | |
| 6,671,534 B2 | 12/2003 | Putz | |
| 6,725,096 B2 | 4/2004 | Chinn et al. | |
| 6,741,892 B1 | 5/2004 | Meadows et al. | |

(Continued)

*Primary Examiner*—Edwin A. Leon
*Assistant Examiner*—Vanessa Girardi
(74) *Attorney, Agent, or Firm*—Fredrikson & Bryon, P.A.

(57) ABSTRACT

An electrical connection assembly of a medical device includes a plurality of electrical contact blocks and a sealing member, which are held within a cavity of a base of the assembly. The sealing member includes a plurality of openings, at least one interior surface surrounding a bore and at least one void. Each electrical contact block extends into a corresponding opening of the sealing member, and a conductive sidewall of each block defines a portion of a perimeter of an area for receiving a lead connector, while the bore of the sealing member forms another portion of the perimeter of the area. The at least one void provides a compressible space in a bulk volume of the sealing member. When the lead is inserted within the area, and a cap is engaged with the base, the at least one interior surface of the sealing member is compressed about the lead.

12 Claims, 6 Drawing Sheets

U.S. PATENT DOCUMENTS 7,134,919 B2 11/2006 Putz
7,402,083 B2 7/2008 Kast et al.
7,425,142 B1 9/2008 Putz

* cited by examiner

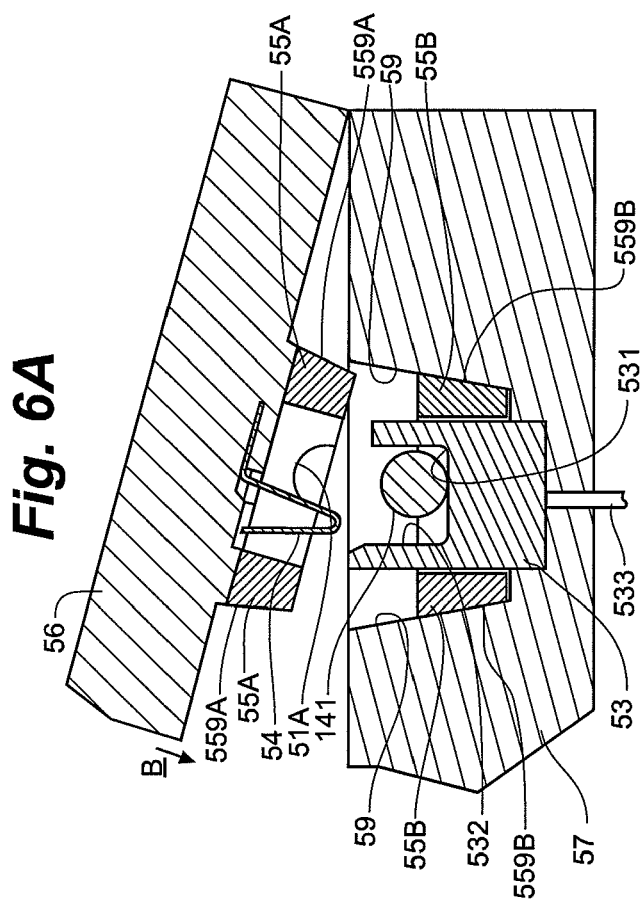
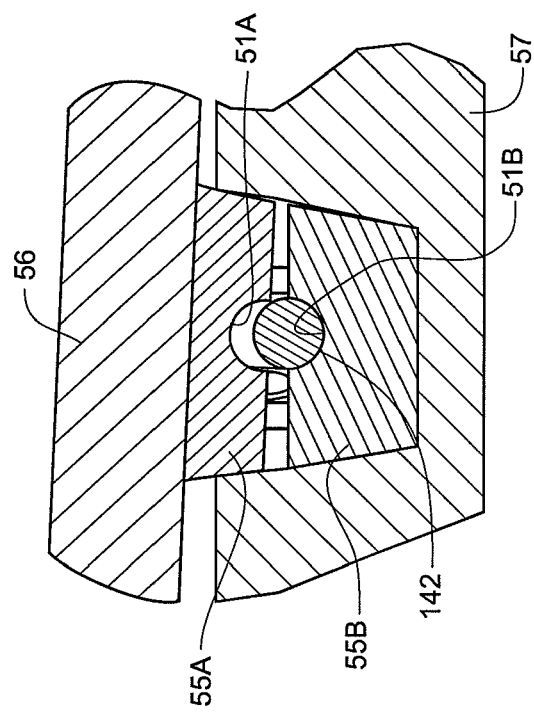
Fig. 6A
Fig. 6B

MEDICAL ELECTRICAL LEAD CONNECTION SYSTEMS AND METHODS

RELATED APPLICATION

This application claims priority to U.S. patent application Ser. No. 12/140,877, which was filed on Jun. 17, 2008, now allowed, which is a continuation of U.S. Pat. No. 7,402,083, which claims priority from U.S. Provisional Patent Application Ser. No. 60/785,194, which was filed on Mar. 23, 2006, all of which applications are hereby incorporated by reference, in their entireties.

TECHNICAL FIELD

The present invention pertains to electrical connection systems, or assemblies, and methods, and more particularly to assemblies and methods facilitating electrical connections of medical electrical leads to medical devices.

BACKGROUND

A host of medical devices include electrical connection assemblies for coupling with a type of medical electrical lead connector that is formed along a proximal portion of the lead and includes a plurality of connector elements disposed along a length thereof. These assemblies typically include a plurality of electrical contacts positioned within an area, or bore, of what is typically called a connector module, or header, at locations corresponding to the connector elements of the lead connector, in order to mate with the corresponding connector elements when the connector is inserted within the bore. Some device connection assemblies further include sealing elements located between the electrical contacts to mate with insulative spacers located between the connector elements of the lead connector, and thereby provide electrical isolation between each mating contact and connector element. Although a variety of connector assembly configurations are known in the art, there is still a need for new methods and assembly designs that provide stable electrical connections, and isolation therebetween, without increasing a force necessary to insert lead connectors into the assembly.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 6A is a cross-section, axial view through an electrical contact portion of the assembly shown in FIG. 5, according to some embodiments.

FIG. 6B is a cross-section, axial view through a non-contact portion of the assembly shown in FIG. 5, according to some embodiments.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1:
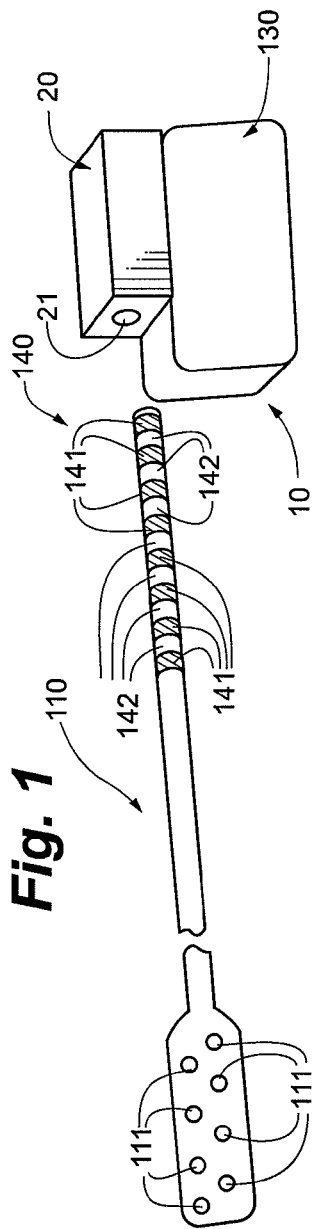
FIG. 1 is a perspective view of a portion of an exemplary medical device system, according to some embodiments of the present invention.
Figure 2:
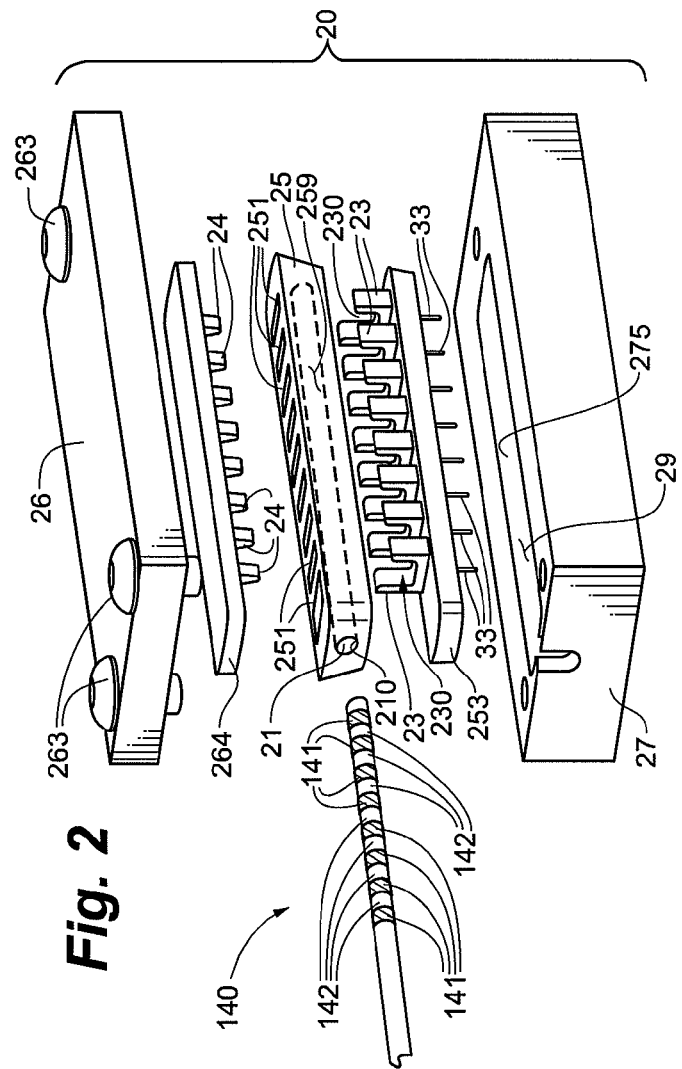
FIG. 2 is an exploded perspective view of an electrical connection assembly, according to some embodiments of the present invention.

FIG. 1 is a perspective view of a portion of an exemplary medical device system 10, according to some embodiments of the present invention. FIG. 1 illustrates system 10 including a medical electrical lead 110 and a medical device 100; a connector 140 of lead 110 is shown terminating a proximal end thereof and including a plurality of connector elements 141 spaced apart along a length of connector 140 by a plurality of insulative spacers 142. Materials and construction methods for lead connectors, such as connector 140 (as well as connector 740, described below), are well known to those skilled in the art. FIG. 1 further illustrates device 100 including a housing 130 and an electrical connection assembly 20, wherein assembly 20 is mounted to housing 130 and includes an area, or bore 21 into which lead connector 140 may be inserted for electrical coupling with circuitry contained within housing 130. FIG. 2 is an exploded perspective view of electrical connection assembly 20, according to some embodiments of the present invention. FIG. 2 illustrates assembly 20 including a module cap 26, a module base 27, a plurality of rigid contact blocks 23 projecting from a foundation 253, a plurality of resilient members 24 projecting from a plate 264, and a bulk sealing member 25 including an interior surface 210 defining a portion of a perimeter of bore 21. Although FIG. 2 shows plate 264 independent of cap 26, it should be noted that plate 264 may be integrally formed with cap 26, or members 24 directly mounted to cap 26. Likewise foundation 253 for blocks 23 may be integral with base 27; however, if base 27 is formed from a conductive material, foundation 253, being formed from a non-conductive material, may be necessary to provide electrical isolation between each of blocks 23. FIG. 2 further illustrates a plurality of feedthrough wires 33, each of which are coupled to a corresponding contact block 23; exemplary materials for wires 33 include, without limitation, tantalum, platinum-iridium (Pt/IR) and niobium. Those skilled in the art will appreciate that, if device 100 is an implantable device, device housing 130 includes a hermetically sealed feedthrough port for each feedthrough wire 33.

Figure 3A:
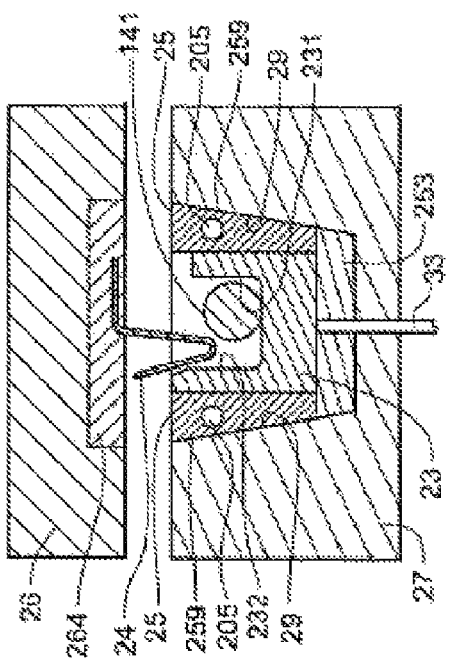
FIG. 3A is a cross-section, axial view through an electrical contact portion of the assembly shown in FIG. 2, according to some embodiments, in an open position.

According to the illustrated embodiment, base 27 includes a cavity 275 for holding sealing member 25 and blocks 23, wherein each block 23, for example, formed from MP35N, Pt/IR, titanium or stainless steel, is mounted in a fixed position within base 27 and extends into a corresponding opening 251 of sealing member 25 such that a groove 230 of each block 23 further defines the perimeter of bore 21, and such that sealing member 25 extends around each block 23 within cavity 275. When cap 26 is brought alongside base 27, each resilient member 24 also extends into a corresponding opening 251 of sealing member 251, for example as is illustrated in FIG. 3A. According to preferred embodiments of the present invention, sealing member 25 is formed from an elastomeric insulative material, preferably silicone rubber, and is held in cavity 275, for example, via an interference fit, without additional securing means, for example, bonding; however the scope of the invention is not so limited, and additional securing means, for example, silicone or polyurethane adhesive, may be used to retain member 25 in cavity 275, according to alternate embodiments.

Figure 3B:
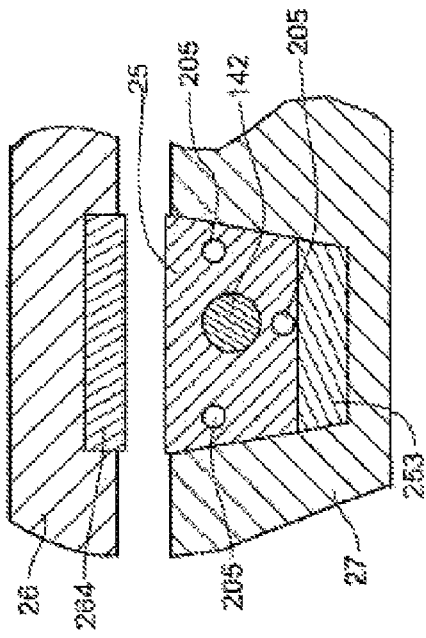
FIG. 3B is a cross-section, axial view through a non-contact portion of the assembly shown in FIG. 2, according to some embodiments, in an open position.
Figure 4A:
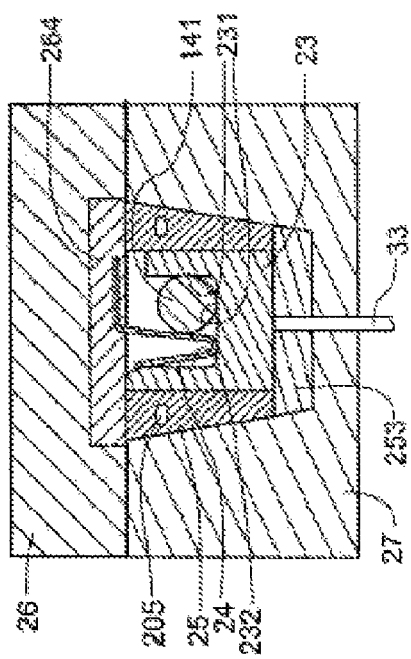
FIG. 4A is a cross-section, axial view through an electrical contact portion of the assembly shown in FIG. 2, according to some embodiments, in a closed position.

FIGS. 3A-B are cross-section, axial views through an electrical contact portion at a location of one of sealing member openings 251, and through a non-contact portion of assembly 20, for example, between two of sealing member openings 251, respectively, according to some embodiments, both with cap 26 in an open position, and both with connector 140 having been axially inserted therein, for example, via arrow A of FIG. 1. FIG. 3A illustrates one of connector elements 141 located within groove 230 of the corresponding block 23, and FIG. 3B illustrates one of insulative spacers 142 located within a portion of bore 21 defined by interior surface 210 of sealing member 25. FIG. 3A further illustrates block 23 including a first sidewall 231 on a first side of groove 230 and a second sidewall 232 on a second side of groove 230; according to the illustrated embodiment, each sidewall 231 is conductive for electrical coupling of the corresponding connector element 141 to the corresponding feedthrough wire 33, when connector 140 is fully inserted within bore 21 such that each connector element 141 is located alongside first groove sidewall 231 of the corresponding block 23. Sidewall 231 may include a surface treatment to enhance surface conductivity, for example, gold sputtering or electroplating, according to some embodiments. When each resilient member 24 is pressed into the corresponding groove 230, alongside the corresponding connector elements 141, for example as illustrated in FIG. 4A, each connector element 141 is forced into electrical contact with conductive sidewall 231 of the corresponding contact block 23. It should be noted that resilient member 24, for example formed as a spring clip, may be conductive, for example, formed from stainless steel, or non-conductive, for example, formed from a polymer coated metal or a creep-resistant resilient plastic, such as PEEK, since members 24 are not required to be conductive in order to facilitate electrical coupling between connector elements 141 and corresponding contact blocks 23 of the illustrated embodiment.

Figure 4B:
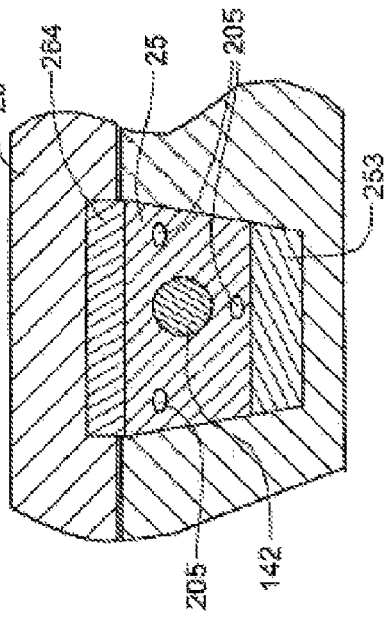
FIG. 4B is a cross-section, axial view through a non-contact portion of the assembly shown in FIG. 2, according to some embodiments, in a closed position.

FIGS. 4A-B are cross-section, axial views, similar to FIGS. 3A-B, but with cap 26 in a closed, or fully engaged position, for example, being secured to base 27 by screws 263 (FIG. 2). With reference back to FIGS. 3A-B, it will be appreciated that, when cap 26 is not fully engaged with base 27, assembly 20 provides sufficient clearance for relatively easy axial insertion of connector 140 into bore 21. FIG. 4A illustrates resilient member 24 being compressed between connector element 241 and groove sidewall 232, thereby applying a spring force that holds connector element 141 against conductive sidewall 231 for stable contact therebetween; and FIG. 4B illustrates the portion of bore 21 defined by interior surface 210 of seal member 25 compressed about insulative spacer 142 to provide electrical isolation between adjacent mating connector elements 141 and contact blocks 23. With reference back to FIG. 1, those skilled in the art will appreciate that an insulated conductor extending within lead 110 electrically couples each connector element 141 to a corresponding electrode 111 so that, when each connector element 141 is coupled, for example, as shown in FIG. 3A, to the corresponding contact block 23, each electrode 111 is electrically coupled to the circuitry contained in device housing 130.

FIGS. 3A-B and 4A-B further illustrate opposing tapered sidewalls 29 of cavity 275 interfacing with tapered outer surfaces 259 of sealing member 25. The interface of corresponding tapers 29, 259 may reduce the force and displacement required to compress sealing member 25 in order to achieve adequate sealing about insulative spacers 142 of lead connector 140, and may further prevent significant distortion of those portions of bore 21 defined by interior surface 210 of sealing member 25. With further reference to FIGS. 3A-B and 4A-B, optional voids 205 are shown formed in sealing member 25; the inclusion of voids 205 in sealing member 25 can allow a volumetric tolerance of member 25 to be opened up, for example, by providing some additional compressible space in a bulk volume thereof; thus, if the bulk volume of sealing member 25 exceeds that of cavity 275, voids 205 can be compressed to effectively reduce the bulk volume of member 25, when cap 26 being is fully engaged with base 27. It should be noted that voids 205 may alternately be located along exterior surfaces of sealing member 25, for example, in the form of grooves extending along sides 259. It should be understood that optional voids 205 are macroscopic and discretely placed by design, as opposed to microscopic and randomly dispersed voids, which might be characteristic of a particular elastomeric material employed by embodiments of the present invention; however, alternate embodiments of the present invention can employ elastomeric materials having microscopic and randomly dispersed voids to provide the compressible space.

Figure 5:
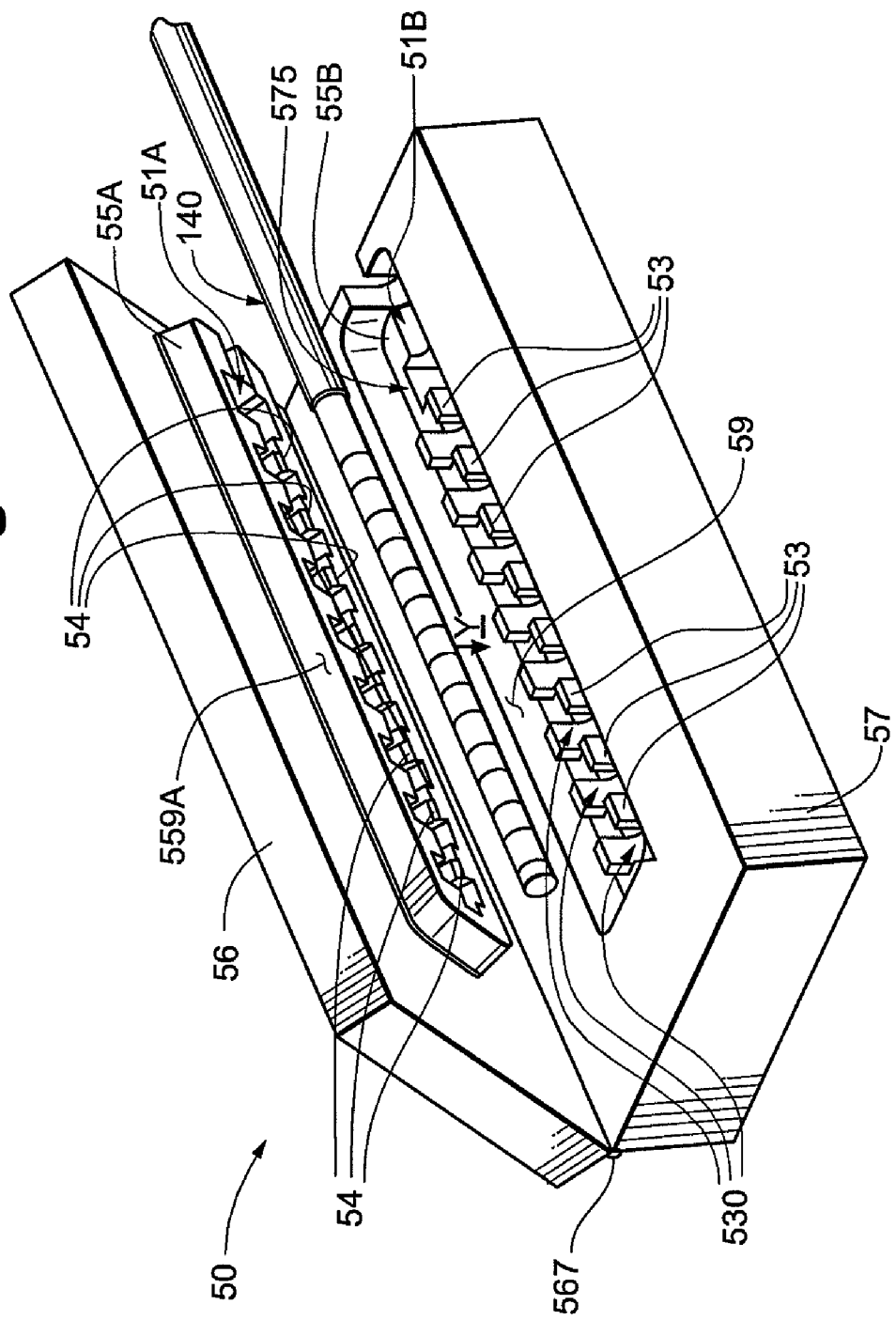
FIG. 5 is a perspective view of an electrical connection assembly, according to some alternate embodiments of the present invention, in an open position.

FIG. 5 is a perspective view of an electrical connection assembly 50, according to some alternate embodiments of the present invention, in an open position to receive a radial, or sideways insertion, for example, via arrow Y, of lead connector 140. FIG. 5 illustrates assembly 50 including a first bulk sealing member 55A and a plurality of resilient members 54 attached to a cap portion 56, and a second bulk sealing member 55B and a plurality of contact blocks 53 held within a cavity 575 of a base portion 57. Like contact blocks 23 of assembly 20, each contact block 53 includes a groove 530, which defines a portion of a perimeter of an area into which lead connector 140 is inserted, per arrow Y. FIG. 5 further illustrates cap 56 attached to base 57 via a hinged coupling 567. When cap 56 is closed over base 57, first sealing member 55A mates with second sealing member 55B and an interior surface 51A of first member 55A combines with an interior surface 55B of second member to define a portion of a bore similar to bore 21 of assembly 20. Like sealing member 25, first and second sealing members 55A,B are formed from an elastomeric insulative material, preferably silicone rubber, and second sealing member 55B is fitted and held within cavity 575 without need for additional securing means, such as bonding, although the scope of the present invention does not preclude additional securing means. First sealing member 55A may be attached to cap 56 by bonding, for example with a silicone or polyurethane adhesive.

FIG. 6A is a cross-section, axial view through an electrical contact portion of assembly 50, according to some embodiments; and FIG. 6B is a cross-section, axial view through a non-contact portion of assembly 50, according to some embodiments. FIG. 6A illustrates one of connector elements 141 of lead connector 140 located in groove 530 of the corresponding contact block 53 and resilient member 54, very similar to member 24 of assembly 20, being brought down, by the closing of cap 56, per arrow B, to be pressed into groove 530, alongside connector element 141, for example, similar to assembly 20, as illustrated in FIG. 4A. As with assembly 20, each connector element 141 is forced into relatively stable electrical contact with a conductive sidewall 531 of the corresponding contact block groove 530 by a spring force of corresponding resilient member 54 being compressed between connector element 141 and an opposing sidewall 532 of groove 230. Resilient member 54 may be formed from any of the materials previously presented for resilient member 24 of assembly 20. FIG. 6A further illustrates one of a plurality of feedthrough wires 533 coupled to contact block 53, and, it should be understood that each contact block 53 is coupled to one of wires 533, similar to blocks 23 and wires 33 of assembly 20, and that blocks 53 and wires 533 may be formed of any of the materials presented for blocks 23 and wires 33, respectively, of assembly 20. FIGS. 6A-6B further illustrate cavity 575 of base 57 including opposing tapered sidewalls 59 to interface with corresponding outer tapered surfaces 559A, B of sealing members 55A,B, which interface may reduce the force and displacement required to compress seal members 55A,B in order to achieve adequate sealing about insulative spacers 142 of lead connector 140. Although not shown, one or both of sealing members 55A,B may include one or more voids formed therein to alleviate volumetric tolerance constraints, as previously described for member 25.

Figure 7:
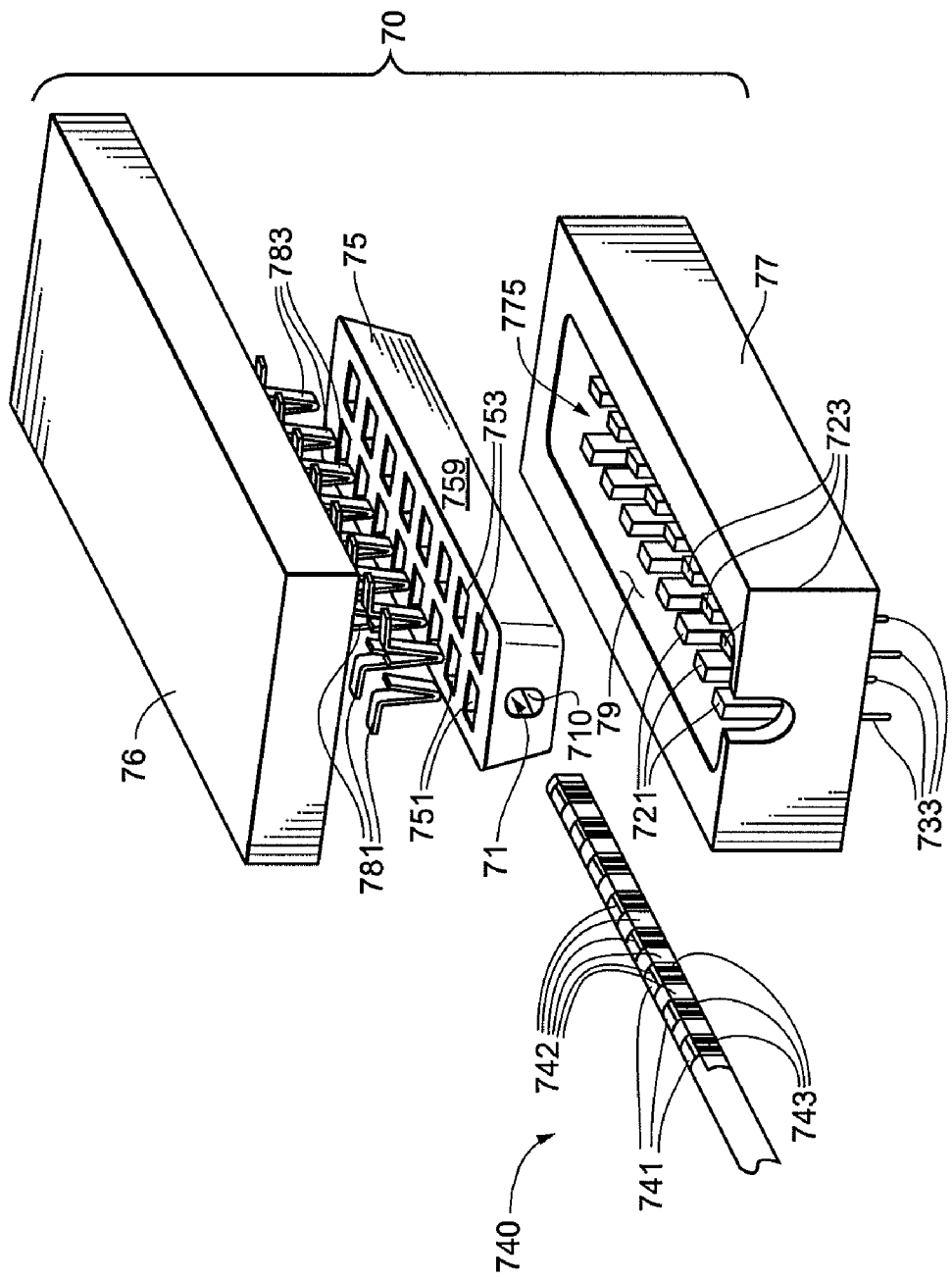
FIG. 7 is an exploded perspective view of an electrical connection assembly, according to yet further embodiments of the present invention.

FIG. 7 is an exploded perspective view of an electrical connection assembly 70, according to yet further embodiments of the present invention, and a corresponding lead connector 740. FIG. 7 illustrates assembly 70 including a cap 76, a base 77, a first column of rigid contact blocks 721, a second column of rigid contact blocks 723 extending alongside the first column, a first column of resilient members 781, a second column of resilient members 783 extending alongside the first column, and a bulk sealing member 75 including an interior surface 710 defining a portion of a perimeter of a bore 71 into which connector 740 may be inserted. Each of resilient members 781, 783 may be a spring clip formed from a conductive material such as stainless steel, Pt/IR, titanium, or MP35N. Likewise rigid contact blocks 721, 723 may be formed from stainless steel, Pt/IR, titanium or MP35N. According to the illustrated embodiment, base 77 includes a cavity 775 for holding blocks 721, 723; each block 721 extends into a corresponding opening 751 of sealing member 75, and each block 723 into a corresponding opening 753 of sealing member 75, so that sealing member 75 extends around each block 721, 723, within cavity 275, and an inner sidewall 701, 703 of each block 721, 723 further defines bore 71.

Figure 8:
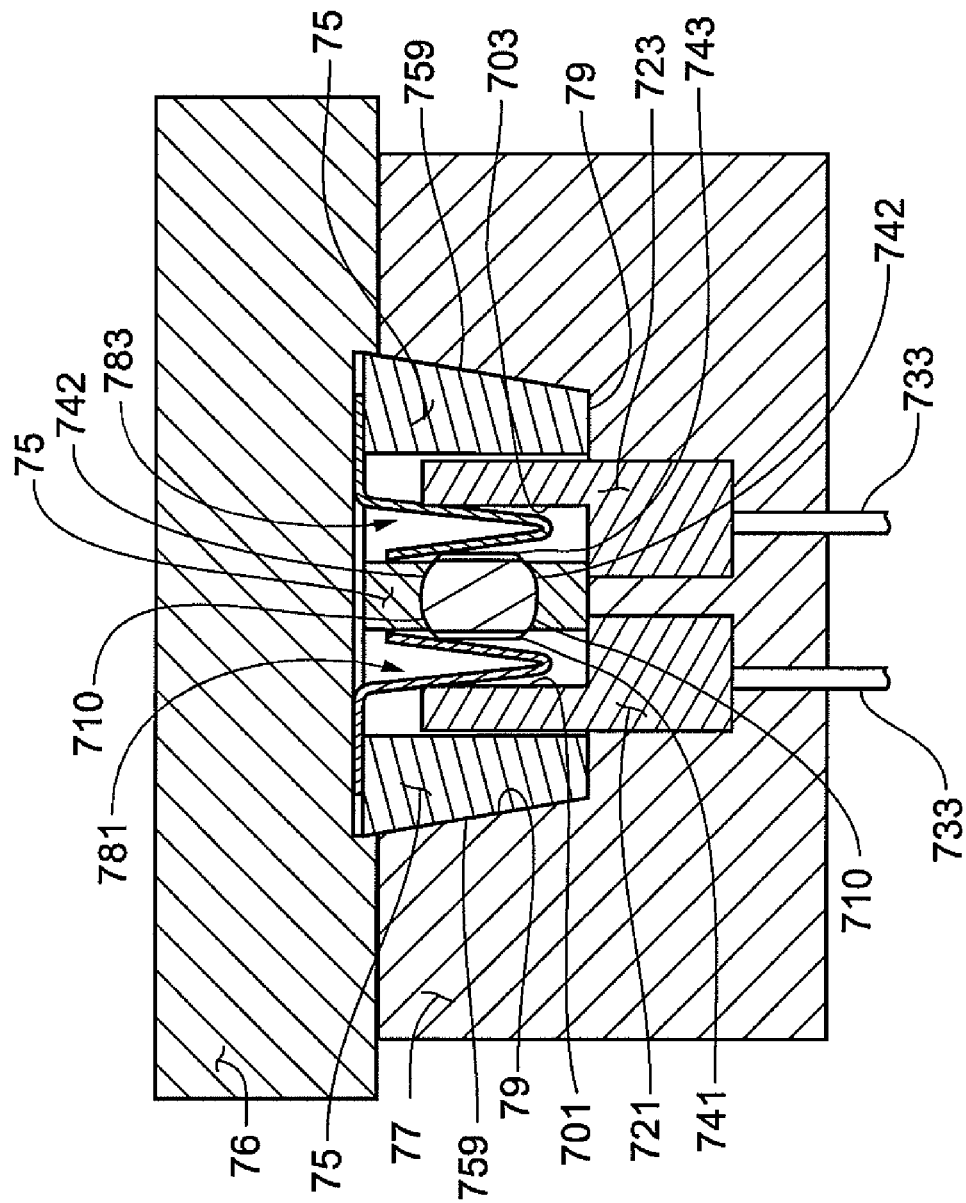
FIG. 8 is a cross-section, axial view through an electrical contact portion of the assembly shown in FIG. 7, according to some embodiments.

FIG. 8 is a cross-section, axial view through an electrical contact portion of assembly 70 at one pair of openings 751, 753, according to some embodiments, wherein connector 740 has been inserted into bore 71 for electrical coupling. FIG. 8 illustrates a feedthrough wire 733, for example, formed from any of the materials previously presented for wires 33, coupled to each of blocks 721, 723; it should be understood that, each of a plurality of wires 733 are coupled to corresponding blocks 721, 723 included in assembly 70. FIGS. 7 and 8 further illustrate connector 741 having what may be designated as a "segmented" construction, wherein a first column of connector elements 741 and a second column of connector elements 743 are spaced apart from one another one either side of a longitudinal axis of connector 741; insulative spacers 742 are shown extending between each column to isolate connector elements 741 from connector elements 743 and between each connector element 741, 743 within each column to isolate the elements in each column from one another. Although surfaces of connector elements 741, 743 are shown being relatively flat, it should be understood that the scope of the present invention is not so limited, and that, according to alternate embodiments, surfaces of elements 741, 743 are curved, for example, extending along a circumference of connector 740.

According to the illustrated embodiment, when cap 76 of assembly 70 is brought into engagement with base 77, each of resilient members 781 is inserted into the corresponding seal member opening 751 and each of resilient members 783 is inserted into the corresponding seal member opening 753 such that each member 781 is compressed between inner sidewall 701 of the corresponding block 721 and the corresponding connector element 741, and each member 783 is compressed between inner sidewall 703 of the corresponding block 723 and the corresponding connector element 743. Thus, when cap 76 is securely engages with base 77, a spring force of each resilient member 781, 783 causes relatively stable electrical coupling between the corresponding connector element 741, 743 and the corresponding sidewall 701, 703, via conductive surfaces of each corresponding resilient member 781, 783. These surfaces of members 781, 783, as well as sidewalls 701, 703, may include surface treatments to enhance conductivity, for example, gold sputtering or electroplating.

FIG. 8 further illustrates opposing tapered sidewalls 79 of cavity 775 interfacing with opposing tapered outer surfaces 759 of sealing member 75, similar to that for assembly 20. Sealing member 75, like sealing member 25 of assembly 20, is formed from an elastomeric insulative material, preferably silicone rubber, an may be retained in cavity 775 without additional securing means. Furthermore, like sealing member 25, although not shown, sealing member 75 may include one or more voids formed therein to alleviate volumetric tolerance constraints, as previously described for member 25. With reference to FIGS. 7 and 8, it will be appreciated that sealing member 75 surrounds each of resilient members 781, 783 and blocks 721,723 and interfaces with insulative spacers 742 of connector 740 to provide electrical isolation, when cap 76 is fully engaged with base 77, between each electrical coupling of connector element 741, 743 to corresponding contact block sidewall 701, 703, via corresponding resilient member 781, 783.

In the foregoing detailed description, the invention has been described with reference to specific embodiments. However, it may be appreciated that various modifications and changes can be made without departing from the scope of the invention as set forth in the appended claims.

We claim:

1. An electrical connection assembly for a medical device, the assembly for coupling the device to a medical electrical lead connector that includes a plurality of connector elements spaced apart from one another along a length of a proximal portion of a medical electrical lead, and the assembly comprising:
   a base for mounting to a housing of the device, the base including a cavity;

a cap engagable with the base;

a bore for receiving insertion of the medical electrical lead connector therein;

a plurality of electrical contact blocks held within the cavity, each of the plurality of electrical contact blocks including a conductive sidewall, the conductive sidewalls defining a portion of a perimeter of the bore and being spaced apart from one another along a length of the bore such that each is located for electrical coupling with a corresponding connector element of the lead connector, when the lead connector is inserted within the bore; and a sealing member held within the base cavity, the sealing member including a plurality of openings, at least one interior surface surrounding the bore, to define another portion of the perimeter of the bore, and at least one void;

wherein each of the plurality of electrical contact blocks extends into a corresponding opening of the plurality of openings of the sealing member;

the at least one void of the sealing member is independent of the bore and of the plurality of openings and provides a compressible space in a bulk volume of the sealing member; and when the lead connector is inserted within the bore and the cap is engaged with the base, the at least one void is compressed and the at least one interior surface of the sealing member is compressed about the lead connector.

2. The assembly of claim 1, further comprising:

another plurality of electrical contact blocks; and wherein each of the two pluralities of electrical contact blocks are arranged in a corresponding column of first and second columns that extend alongside one another, so that each electrical contact block of both pluralities extends into the corresponding opening of the plurality of openings of the sealing member;

each electrical contact block of the other plurality also includes a conductive sidewall that defines yet another portion of a perimeter of the bore; and the conductive sidewalls of the other plurality of electrical contact blocks are also spaced apart from one another along the length of the bore such that each is located for electrical coupling with a corresponding connector element of the lead connector, when the lead connector is inserted within the bore.

3. The assembly of claim 2, further comprising:

a plurality of resilient members attached to the cap and arranged in first and second columns that extend alongside one another, the first column of resilient members corresponding to the first column of the plurality of electrical contact blocks and the second column of resilient members corresponding to the second column of the other plurality of electrical contact blocks so that each resilient member of each of the first and second columns is positioned for applying a spring force against a corresponding conductive sidewall within the corresponding opening of the plurality of openings of the sealing member, when the cap is engaged with the base; and wherein, when lead connector is inserted within the bore and the cap is engaged with the base, each resilient member of the first column of the plurality of resilient members applies a spring force against both the conductive sidewall of the corresponding contact block of the first column thereof and a corresponding connector element of the inserted lead connector, to cause electrical coupling between each corresponding conductive sidewall of the first column and each connector element, and each resilient member of the second column of the plurality of resilient members applies a spring force against both the conductive sidewall of the corresponding contact block of the second column thereof and against a corresponding connector element of the inserted lead connector, to cause electrical coupling between each corresponding conductive sidewall of the second column and each connector element; and each resilient member of the first and second columns includes a conductive surface, and the spring force applied by each resilient member urges the conductive surface of the member into contact with the corresponding conductive sidewall and corresponding connector element, to cause the electrical coupling for each connector element of the inserted lead connector.

4. The assembly of claim 1, further comprising:

a plurality of resilient members attached to the cap, each member applying a spring force against a corresponding connector element of the lead connector, when the lead connector is inserted within the bore so that each connector element of the plurality of connector elements is positioned adjacent to the corresponding conductive sidewall, and when the cap is engaged with the base; and wherein the applied spring force of each resilient member causes electrical coupling between the corresponding connector element and the corresponding conductive sidewall.

5. The assembly of claim 4, wherein the spring force of each resilient member urges the corresponding connector element into contact with the corresponding conductive sidewall to cause the electrical coupling.

6. The assembly of claim 4, wherein each resilient member further includes a conductive surface and the spring force of each resilient member urges the conductive surface of the member into contact with the corresponding connector element and the corresponding conductive sidewall to cause the electrical coupling.

7. A medical device configured for coupling to a medical electrical lead connector that includes a plurality of connector elements spaced apart from one another along a length of a proximal portion of a medical electrical lead, and the medical device comprising:

a housing containing electronic circuitry;

a base mounted to the housing and including a cavity;

a cap engagable with the base;

a bore for receiving insertion of the medical electrical lead connector therein;

a plurality of electrical contact blocks held within the cavity, each of the plurality of electrical contact blocks including a conductive sidewall, the conductive sidewalls defining a portion of a perimeter of the bore and being spaced apart from one another along a length of the bore such that each is located for electrical coupling with a corresponding connector element of the lead connector, when the lead connector is inserted within the bore;

a plurality of feedthrough wires, each of the plurality of feedthrough wires being electrically coupled to a corresponding electrical contact block of the plurality of contact blocks and extending through the base and into the housing for electrical coupling with the circuitry contained therein;

a sealing member held within the base cavity, the sealing member including a plurality of openings, at least one interior surface surrounding the bore, to define another portion of the perimeter of the bore, and at least one void;

wherein each of the plurality of electrical contact blocks extends into a corresponding opening of the plurality of openings of the sealing member;

the at least one void of the sealing member is independent of the bore and of the plurality of openings and provides a compressible space in a bulk volume of the sealing member; and when the lead connector is inserted within the bore and the cap is engaged with the base, the at least one void is compressed and the at least one interior surface of the sealing member is compressed about the lead connector.

8. The device of claim 7, further comprising:

another plurality of electrical contact blocks; and another plurality of feedthrough wires, each of the other plurality of feedthrough wires being electrically coupled to a corresponding electrical contact block of the other plurality of contact blocks and extending through the base and into the housing for electrical coupling with the circuitry contained therein; and wherein each of the two pluralities of electrical contact blocks are arranged in a corresponding column of first and second columns that extend alongside one another, so that each electrical contact block of both pluralities extends into the corresponding opening of the plurality of openings of the sealing member;

each electrical contact block of the other plurality also includes a conductive sidewall that defines yet another portion of a perimeter of the bore; and the conductive sidewalls of the other plurality of electrical contact blocks are also spaced apart from one another along the length of the bore such that each is located for electrical coupling with a corresponding connector element of the lead connector, when the lead connector is inserted within the bore.

9. The device of claim 8, further comprising:

a plurality of resilient members attached to the cap and arranged in first and second columns that extend alongside one another, the first column of resilient members corresponding to the first column of the plurality of electrical contact blocks and the second column of resilient members corresponding to the second column of the other plurality of electrical contact blocks so that each resilient member of each of the first and second columns is positioned for applying a spring force against a corresponding conductive sidewall within the corresponding opening of the plurality of openings of the sealing member, when the cap is engaged with the base; and wherein, when lead connector is inserted within the bore and the cap is engaged with the base, each resilient member of the first column of the plurality of resilient members applies a spring force against both the conductive sidewall of the corresponding contact block of the first column thereof and a corresponding connector element of the inserted lead connector, to cause electrical coupling between each corresponding conductive sidewall of the first column and each connector element, and each resilient member of the second column of the plurality of resilient members applies a spring force against both the conductive sidewall of the corresponding contact block of the second column thereof and against a corresponding connector element of the inserted lead connector, to cause electrical coupling between each corresponding conductive sidewall of the second column and each connector element; and each resilient member of the first and second columns includes a conductive surface, and the spring force applied by each resilient member urges the conductive surface of the member into contact with the corresponding conductive sidewall and corresponding connector element, to cause the electrical coupling for each connector element of the inserted lead connector.

10. The device of claim 7, further comprising:

a plurality of resilient members attached to the cap, each member applying a spring force against a corresponding connector element of the lead connector, when the lead connector is inserted within the bore so that each connector element of the plurality of connector elements is positioned adjacent to the corresponding conductive sidewall, and when the cap is engaged with the base; and wherein the applied spring force of each resilient member causes electrical coupling between the corresponding connector element and the corresponding conductive sidewall.

11. The device of claim 10, wherein the spring force of each resilient member urges the corresponding connector element into contact with the corresponding conductive sidewall to cause the electrical coupling.

12. The device of claim 10, wherein each resilient member further includes a conductive surface and the spring force of each resilient member urges the conductive surface of the member into contact with the corresponding connector element and the corresponding conductive sidewall to cause the electrical coupling.

* * * * *